(12) United States Patent
Fernandez

(10) Patent No.: US 11,844,888 B1
(45) Date of Patent: Dec. 19, 2023

(54) PHOTONIC CORPUSCULAR IRRADIATOR MACHINE

(71) Applicant: Danilo O. Fernandez, Miami, FL (US)

(72) Inventor: Danilo O. Fernandez, Miami, FL (US)

( * ) Notice: Subject to any disclaimer, the term of this patent is extended or adjusted under 35 U.S.C. 154(b) by 532 days.

(21) Appl. No.: 17/199,997

(22) Filed: Mar. 12, 2021

(51) Int. Cl.
*A61L 2/00* (2006.01)
*A61L 2/26* (2006.01)
*A61M 1/02* (2006.01)

(52) U.S. Cl.
CPC ......... *A61M 1/0259* (2013.01); *A61L 2/0047* (2013.01); *A61L 2/26* (2013.01); *A61M 1/0209* (2013.01); *A61L 2202/11* (2013.01); *A61L 2202/121* (2013.01); *A61L 2202/122* (2013.01); *A61L 2202/123* (2013.01); *A61L 2202/22* (2013.01)

(58) Field of Classification Search
CPC ...... A61L 2/0047; A61L 2/26; A61L 2202/11; A61L 2202/121; A61L 2202/122; A61L 2202/123; A61L 2202/22; A61M 1/0259; A61M 1/0209
See application file for complete search history.

(56) References Cited

U.S. PATENT DOCUMENTS

| 1,683,877 | A |  | 9/1928 | Edblom et al. |
|---|---|---|---|---|
| 5,562,836 | A | * | 10/1996 | Joie ........................ B01D 21/34 604/408 |
| 9,208,296 | B1 | * | 12/2015 | Romanick ........... A61M 1/3621 |
| 2003/0165398 | A1 | * | 9/2003 | Waldo ..................... A61L 2/087 604/20 |
| 2017/0021042 | A1 | * | 1/2017 | Dodd .................. A61M 1/3681 |
| 2017/0029776 | A1 | * | 2/2017 | Cork .................... A61M 1/3681 |

* cited by examiner

*Primary Examiner* — Sean M Luck
(74) *Attorney, Agent, or Firm* — Albert Bordas, P.A.

(57) ABSTRACT

A photonic corpuscular irradiator machine, having an irradiation chamber having an external wall, a top edge, a bottom edge, an internal wall, and a spiral ridge; and an ultraviolet irradiation lamp. A machine assembly has an irradiation chamber housing, a bar code scanner, a control panel, an automatic peristaltic pump, and an intensity dial; and further having first and second blood bags. The external wall and the internal wall define a peripheral channel between them, and the spiral ridge extends within the peripheral channel. Blood from the first blood bag travels through an inlet port and is forced upwardly in a spiral motion along the spiral ridge within the peripheral channel and exits from an outlet port to the second bag. The irradiation bulb within of the cavity irradiates ultraviolet light to the blood within the peripheral channel. The ultraviolet light treats blood containing COVID-19 and/or pathogens.

20 Claims, 5 Drawing Sheets

US 11,844,888 B1

PHOTONIC CORPUSCULAR IRRADIATOR MACHINE

BACKGROUND OF THE INVENTION

1. Field of the Invention

The present invention relates to medical devices, and more particularly, to photonic corpuscular irradiator machines for blood irradiation.

2. Description of the Related Art

Applicant believes that one of the closest references corresponds to U.S. Pat. No. 1,683,877 issued to L. A. Edblom et al. on Sep. 11, 1928 for Means for treating blood stream infections. However, it differs from the present invention because L. A. Edblom et al. teaches a method and means for treating blood stream infections and other pathologic blood conditions.

Other patents describing the closest subject matter provide for a number of more or less complicated features that fail to solve the problem in an efficient and economical way. None of these patents suggest the novel features of the present invention.

SUMMARY OF THE INVENTION

The present invention is a photonic corpuscular irradiator machine, comprising an irradiation chamber having an external wall, a top edge, a bottom edge, an internal wall, and a spiral ridge; and an ultraviolet irradiation lamp. A machine assembly comprises an irradiation chamber housing, a bar code scanner, a control panel, an automatic peristaltic pump, and an intensity dial; and further comprising first and second blood bags.

The irradiation chamber further comprises a cap and a base, and defines a cavity. The irradiation chamber further comprises an inlet port and an outlet port. The irradiation chamber is cylindrical in shape. The external wall and the internal wall define a peripheral channel between them, and the spiral ridge extends within the peripheral channel. The cap comprises a cap groove to receive an O-ring. The base comprises a base groove to receive an O-ring. Adjacent to the base, the inlet port extends outwardly from the exterior wall, and adjacent to the top edge, the outlet port extends outwardly from the exterior wall. The inlet port and the outlet port are positioned at opposite sides of the exterior wall, and the inlet port and the outlet port connect to the peripheral channel.

The ultraviolet irradiation lamp comprises an irradiation bulb and a bulb base. The cavity and the irradiation bulb are cylindrical in shape. The cavity receives the irradiation bulb. The cavity has a first predetermined diameter and the irradiation bulb has a second predetermined diameter, whereby the first predetermined diameter is larger than the second predetermined diameter.

The machine assembly further comprises a front side, a back side, first and second doors, first and second rails, a door lock, a Liquid Crystal Display, a memory card port, and a keyboard. The irradiation chamber housing comprises a housing base and a lid having first and second lateral walls. The irradiation chamber is positioned on the housing base and the lid covers the irradiation chamber. The first blood bag has a first intravenous spike extension kit and an inlet tubing connected to the inlet port, and the second blood bag has a second intravenous spike extension kit and an outlet tubing connected to the outlet port.

Blood from the first blood bag travels through the inlet port and is forced upwardly in a spiral motion along the spiral ridge within the peripheral channel and exits from the outlet port to the second bag. The irradiation bulb within of the cavity irradiates ultraviolet light to the blood within the peripheral channel. The ultraviolet light treats blood containing COVID-19 and/or pathogens.

It is therefore one of the main objects of the present invention to provide a photonic corpuscular irradiator machine.

It is another object of this invention to provide a photonic corpuscular irradiator machine for hemoirradiation therapy.

It is another object of this invention to provide a photonic corpuscular irradiator machine to destroy viruses and other pathogens using Ultra Violet irradiation.

It is another object of this invention to provide a photonic corpuscular irradiator machine for COVID-19 and multiple pathogens treatment.

It is another object of this invention to provide a photonic corpuscular irradiator machine that is volumetrically efficient for carrying, transporting, and storage.

It is another object of this invention to provide a photonic corpuscular irradiator machine, which is of a durable and reliable construction.

It is yet another object of this invention to provide a photonic corpuscular irradiator machine that is inexpensive to manufacture and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE PREFERRED EMBODIMENT

Figure 1:
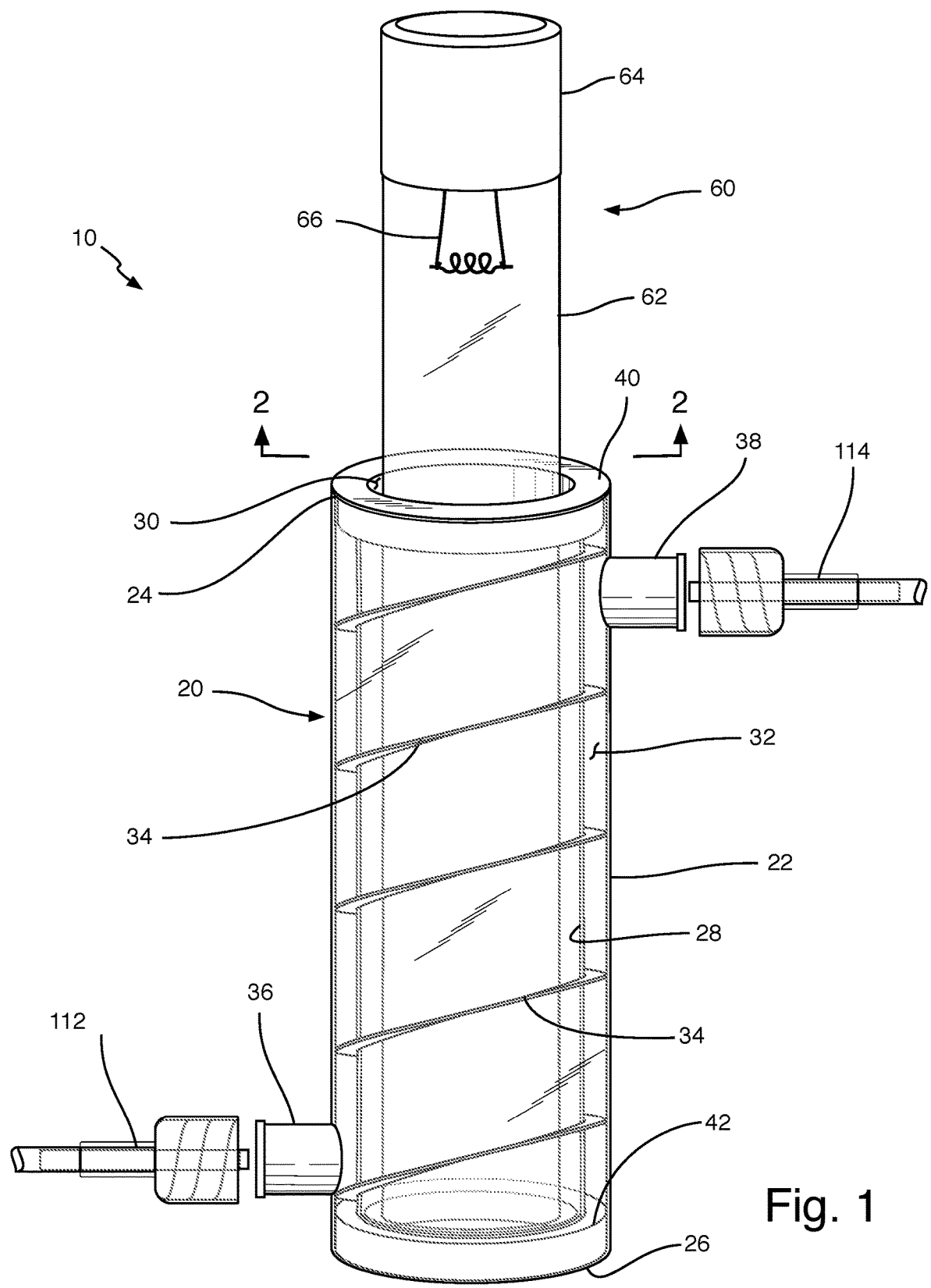
FIG. 1 is an isometric view of an irradiation chamber and an Ultra Violet irradiation lamp of the present invention.

Referring now to the drawings, the present invention is a photonic corpuscular irradiator machine, and is generally referred to with numeral 10. It can be observed that it basically includes irradiation chamber 20, ultraviolet irradiation lamp 60, and machine assembly 100.

Figure 2:
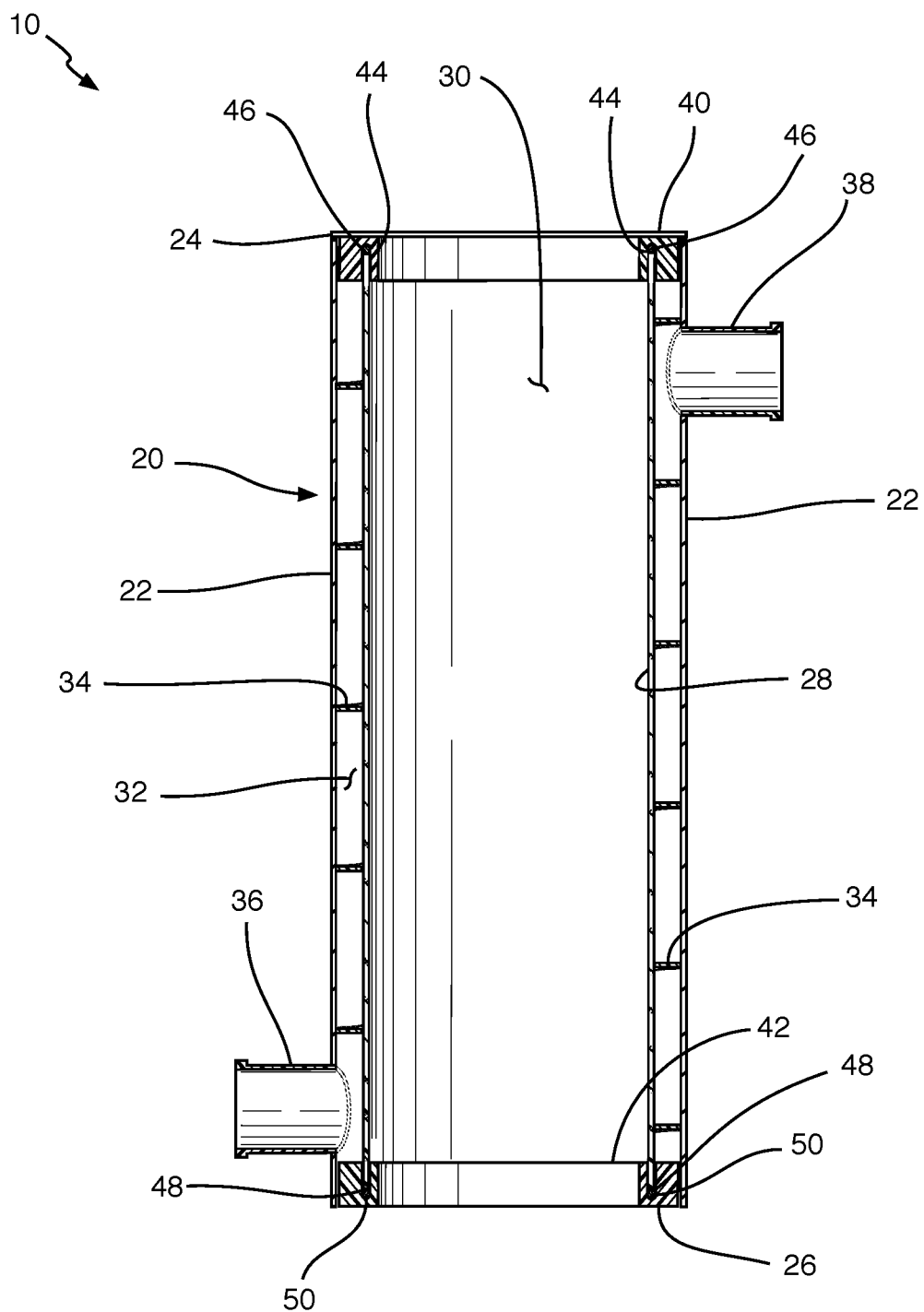
FIG. 2 is a cut view taken along lines 2-2 from FIG. 1.

As seen in FIGS. 1 and 2, irradiation chamber 20 comprises external wall 22, top edge 24, bottom edge 26, internal wall 28, and spiral ridge 34. Irradiation chamber 20 further comprises inlet port 36, outlet port 38, cap 40, and base 42. Irradiation chamber 20 is cylindrical in shape. External wall 22 and internal wall 28 define peripheral channel 32 between them, and spiral ridge 34 extends within peripheral channel 32. In a preferred embodiment, internal wall 28 is made of quartz glass, defines cavity 30, and is biased against spiral ridge 34. Adjacent to base 42, inlet port 36 extends outwardly from exterior wall 22, and adjacent to top edge 24, outlet port 38 extends outwardly from exterior wall 22. In a preferred embodiment, inlet port 36 and outlet port 38 are positioned at opposite sides of exterior wall 22, and inlet port 36 and outlet port 38 connect to peripheral channel 32.

As seen in FIG. 2, cap 40 comprises cap groove 44 to receive O-ring 46, and base 42 comprises base groove 48 to receive O-ring 50. Internal wall 28, ideally of quartz glass or any glass having similar characteristics, is positioned within irradiation chamber assembly 20, wherein a lower end of internal wall 28 is inserted in base groove 48 having O-ring 50, and an upper end of internal wall 28 is inserted into cap groove 44 having O-ring 46 to prevent blood leakage. It is noted that cap 40 and base 42 are hermetically sealed to prevent spillage/leakage of blood, and/or contamination to the blood. In a preferred embodiment, cap 40 and base 42 are ultrasonically welded to make irradiation chamber assembly 20 hermetically sealed.

Figure 3:
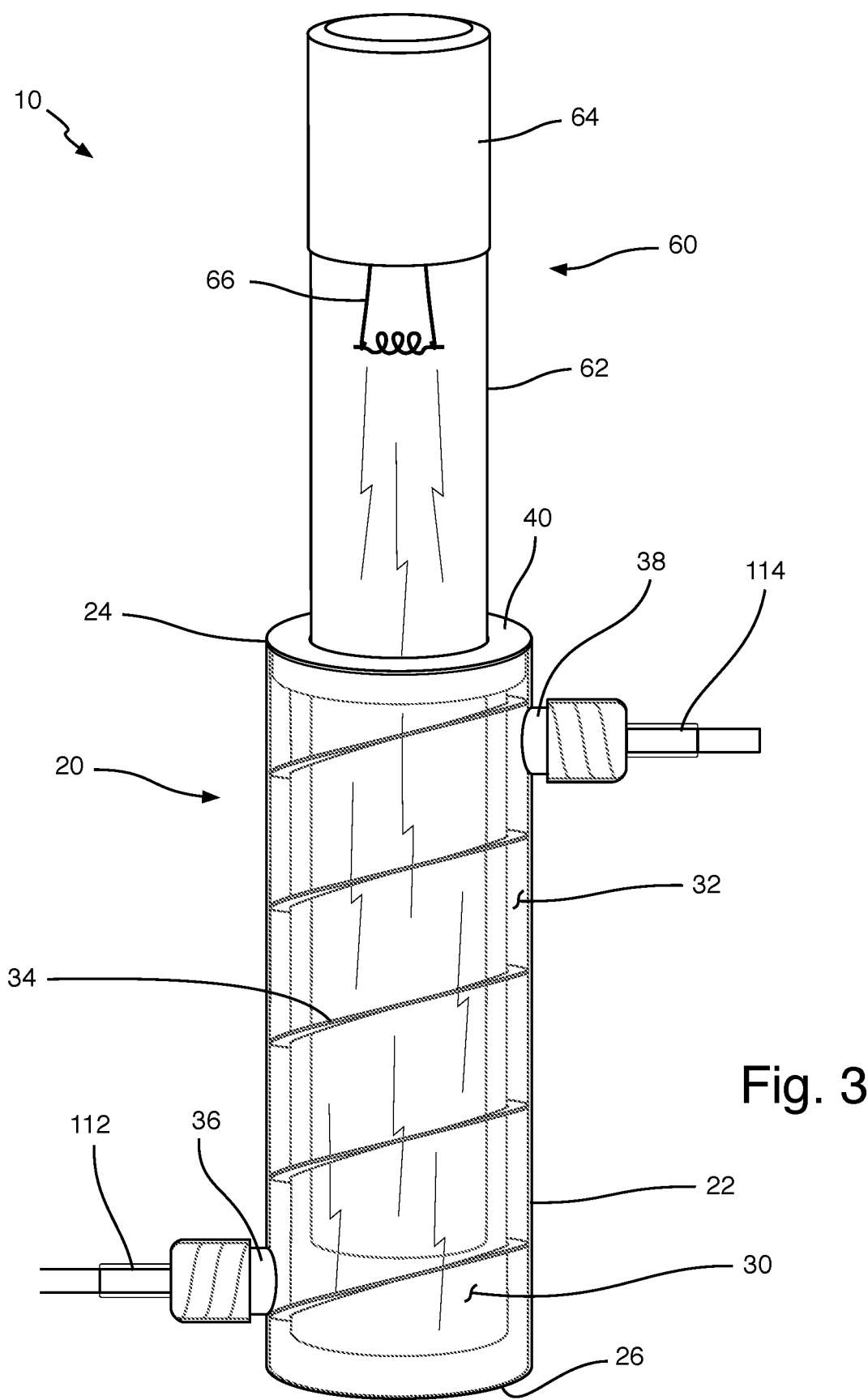
FIG. 3 is an isometric view of the irradiation chamber and the Ultra Violet irradiation lamp, in which the Ultra Violet irradiation lamp is being positioned inside of the irradiation chamber.

As seen in FIG. 3, ultraviolet irradiation lamp 60 is being inserted inside of irradiation chamber 20. Ultraviolet irradiation lamp 60 comprises irradiation bulb 62, bulb base 64, and filaments 66. It is noted however that ultraviolet irradiation lamp 60 can be any lamp or bulb that irradiates ultraviolet light. Cavity 30 and irradiation bulb 62 are cylindrical in shape. Cavity 30 snugly receives irradiation bulb 62, whereby cavity 30 has a first predetermined diameter and irradiation bulb 62 has a second predetermined diameter, and the first predetermined diameter is slightly larger than the second predetermined diameter. It is noted that for use, ultraviolet irradiation lamp 60 is inserted inside of irradiation chamber 20 until its bottom end is biased against base 42, seen in FIG. 2.

Figure 4:
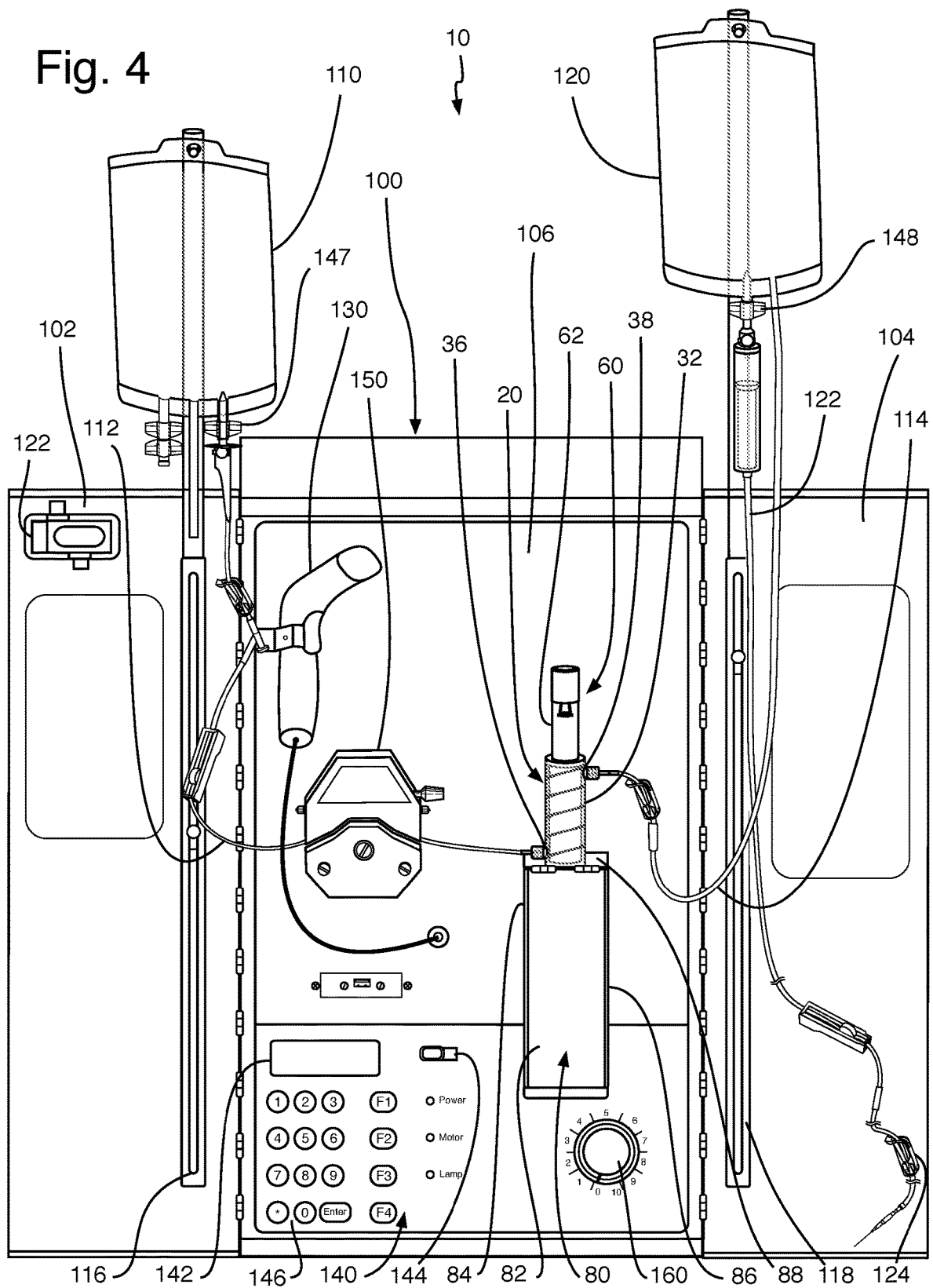
FIG. 4 is a front view of the present invention.
Figure 5:
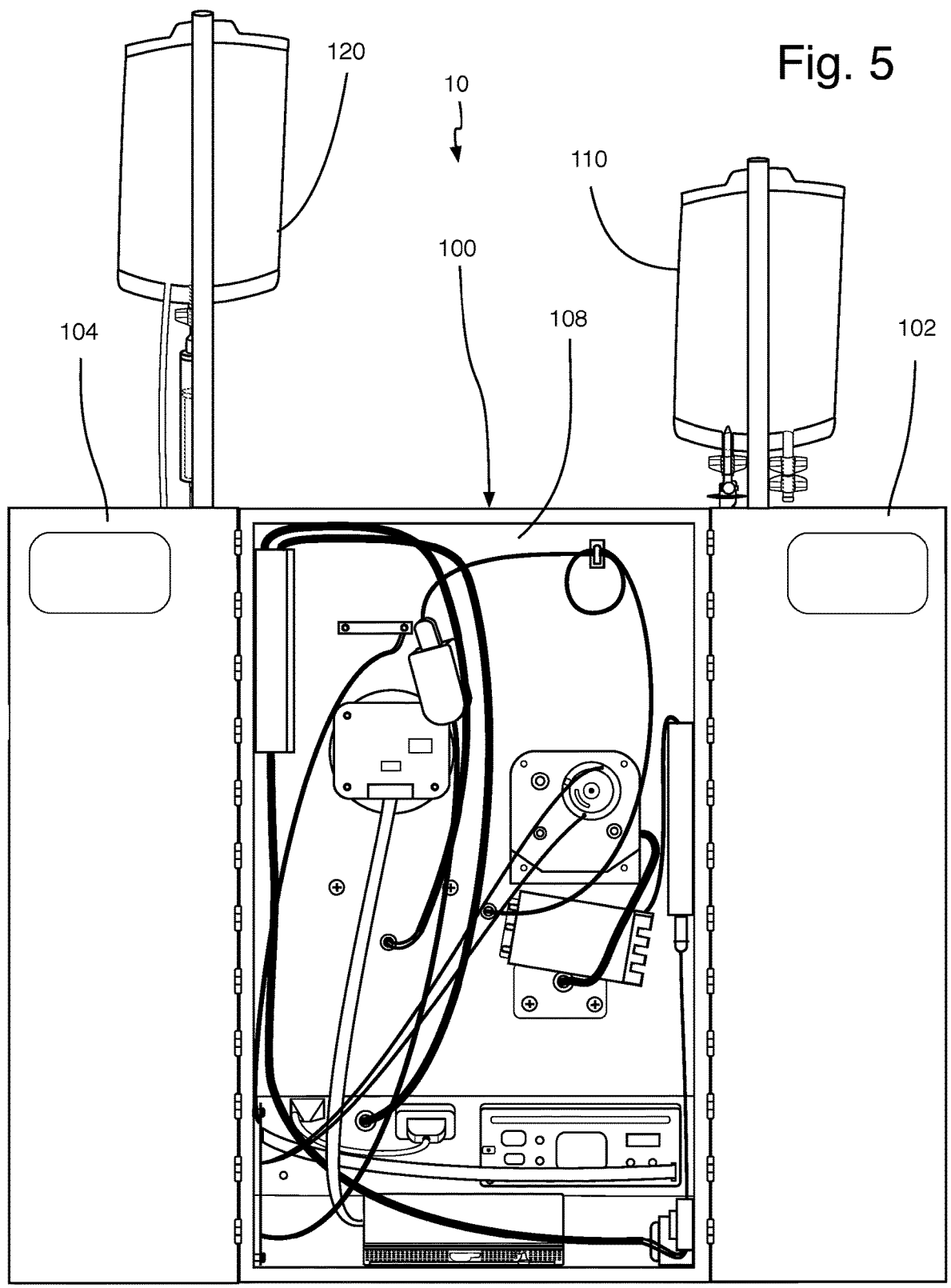
FIG. 5 is a rear view of the present invention.

As seen in FIGS. 4 and 5, machine assembly 100 comprises first door 102, second door 104, front side 106, and back side 108. Front side 106 comprises irradiation chamber housing 80, bar code scanner 130, control panel 140, automatic peristaltic pump 150, and intensity dial 160. Irradiation chamber housing 80 comprises housing base 88 and lid 82. Lid 82 has first lateral wall 84 with slot 90, and second lateral wall 86 with slot 92. Irradiation chamber 20 is positioned onto housing base 88. For illustrative purposes, lid 82 is in an open position. However, it is understood that in operation, lid 82 is in a closed position to cover irradiation chamber 20 while irradiating ultraviolet light, whereby slot 90 receives/accommodates inlet tubing 112, and slot 92 receives/accommodates outlet tubing 114, to permit lid 82 to properly close. In the preferred embodiment, control panel 140 comprises Liquid Crystal Display (LCD) 142, and memory card port 144. In one embodiment, control panel 140 comprises keyboard 146. Other embodiments for control panel 140 may consist of a touch screen. In a preferred embodiment, memory card port 144 receives an intelliflash-card. In another embodiment, memory card port 144 may be incorporated to control panel 140, when the touch screen embodiment is used instead.

Machine assembly 100 further comprises first blood bag 110 and second blood bag 120. Door 102 comprises rail 116 and door lock 122. Door 104 comprises rail 118. Rails 116 and 118 are vertically adjustable to hold blood bags 110 and 120 respectively. First blood bag 110 has intravenous (IV) spike extension kit 147, and inlet tubing 112 that connects to inlet port 36. Second blood bag 120 has intravenous (IV) spike extension kit 148, and outlet tubing 114 connected to outlet port 38. Extending from second blood bag 120, is blood exit tubing 126 having three-way catheter 124.

In operation, blood from a patient is collected in first blood bag 110. With automatic peristaltic pump 150 operating, the blood from first blood bag 110 travels through IV spike extension kit 147 and inlet tubing 112, a section of which is inserted within automatic peristaltic pump 150, and connects to inlet port 36. Referring to FIG. 3, the blood then travels through inlet port 36 and is forced upwardly in a spiral motion along spiral ridge 34 within peripheral channel 32. Irradiation bulb 62 rests inside cavity of irradiation chamber assembly 20, as seen in FIG. 4. Referring to FIG. 3, irradiation bulb 62 irradiates ultraviolet light outwardly through internal wall 28, irradiating the blood flowing within peripheral channel 32, as it is being forced upwardly by automatic peristaltic pump 150 towards outlet port 38.

In one embodiment, peripheral channel 32 is approximately 0.1-5.0 mm in width to ensure that the blood is effectively radiated as it is being forced upwardly in the spiral motion along spiral ridge 34 within peripheral channel 32. In a preferred embodiment, peripheral channel 32 is approximately 1.0-3.0 mm in width to ensure that the blood is effectively radiated as it is being forced upwardly in the spiral motion along spiral ridge 34 within peripheral channel 32.

It is understood that a flow rate of automatic peristaltic pump 150 is adequate to ensure that the blood is effectively radiated as it is being forced upwardly in the spiral motion along spiral ridge 34 within peripheral channel 32.

Furthermore, it is understood that ultraviolet irradiation lamp 60 operates at a safe and sufficient wattage to ensure that the blood is effectively radiated as it is being forced upwardly in the spiral motion along spiral ridge 34 within peripheral channel 32.

Irradiated blood then travels from outlet port 38 through outlet tubing 114 to second blood bag 120 having intravenous (IV) spike extension kit 148. The irradiated blood is then re-infused into a patient via three-way catheter 124. In the preferred embodiment, intensity dial 160 is configured with numbers, as an example from 0-10, to adjust radiation intensities. In another embodiment, intensity dial 160 may be incorporated to control panel 140, when the touch screen embodiment is used instead.

In a preferred embodiment, inlet tubing 112 and outlet tubing 114 are twelve-inch silicone tubes.

Present invention 10 is used for the treatment of multiple diseases through Ultra Violet irradiation. The curative properties in vivo are derived from the activation, excitation, and stimulatory effect upon cells and molecules, which compose human blood. Present invention 10 is also used to treat multiple pathogenic infections and diseases like, but not limited to, the following: HIV/AIDS, Leishmaniasis, Dengue, Malaria, Zika Virus, and Necrotizing Fasciitis caused by Group A Streptococcus (GAS) bacteria. In a preferred embodiment, present invention 10 is used for the treatment of coronaviruses, specifically COVID-19.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A photonic corpuscular irradiator machine, comprising:
   A) an irradiation chamber having an external wall, a top edge, a bottom edge, an internal wall, and a spiral ridge;
   B) an ultraviolet irradiation lamp;

C) a machine assembly comprising an irradiation chamber housing, a bar code scanner, a control panel, an automatic peristaltic pump, and an intensity dial; and D) first and second blood bags.

2. The photonic corpuscular irradiator machine set forth in claim 1, further characterized in that said irradiation chamber further comprises a cap and a base, and defines a cavity.

3. The photonic corpuscular irradiator machine set forth in claim 2, further characterized in that said irradiation chamber further comprises an inlet port and an outlet port.

4. The photonic corpuscular irradiator machine set forth in claim 1, further characterized in that said irradiation chamber is cylindrical in shape.

5. The photonic corpuscular irradiator machine set forth in claim 3, further characterized in that said external wall and said internal wall define a peripheral channel between them, and said spiral ridge extends within said peripheral channel.

6. The photonic corpuscular irradiator machine set forth in claim 2, further characterized in that said cap comprises a cap groove to receive an O-ring.

7. The photonic corpuscular irradiator machine set forth in claim 2, further characterized in that said base comprises a base groove to receive an O-ring.

8. The photonic corpuscular irradiator machine set forth in claim 3, further characterized in that adjacent to said base, said inlet port extends outwardly from said exterior wall, and adjacent to said top edge, said outlet port extends outwardly from said exterior wall.

9. The photonic corpuscular irradiator machine set forth in claim 5, further characterized in that said inlet port and said outlet port are positioned at opposite sides of said exterior wall, and said inlet port and said outlet port connect to said peripheral channel.

10. The photonic corpuscular irradiator machine set forth in claim 5, further characterized in that said ultraviolet irradiation lamp comprises an irradiation bulb and a bulb base.

11. The photonic corpuscular irradiator machine set forth in claim 10, further characterized in that said cavity and said irradiation bulb are cylindrical in shape.

12. The photonic corpuscular irradiator machine set forth in claim 10, further characterized in that said cavity receives said irradiation bulb.

13. The photonic corpuscular irradiator machine set forth in claim 10, further characterized in that said cavity has a first predetermined diameter and said irradiation bulb has a second predetermined diameter, whereby said first predetermined diameter is larger than said second predetermined diameter.

14. The photonic corpuscular irradiator machine set forth in claim 1, further characterized in that said machine assembly further comprises a front side, a back side, first and second doors, first and second rails, a door lock, a Liquid Crystal Display, and a memory card port.

15. The photonic corpuscular irradiator machine set forth in claim 1, further characterized in that said irradiation chamber housing comprises a housing base and a lid having first and second lateral walls.

16. The photonic corpuscular irradiator machine set forth in claim 15, further characterized in that said irradiation chamber is positioned on said housing base and said lid covers said irradiation chamber.

17. The photonic corpuscular irradiator machine set forth in claim 5, further characterized in that said first blood bag has a first intravenous spike extension kit and an inlet tubing connected to said inlet port, and said second blood bag has a second intravenous spike extension kit and an outlet tubing connected to said outlet port.

18. The photonic corpuscular irradiator machine set forth in claim 17, further characterized in that blood from said first blood bag travels through said inlet port and is forced upwardly in a spiral motion along said spiral ridge within said peripheral channel and exits from said outlet port to said second bag.

19. The photonic corpuscular irradiator machine set forth in claim 17, further characterized in that said irradiation bulb within of said cavity irradiates ultraviolet light to said blood within said peripheral channel.

20. The photonic corpuscular irradiator machine set forth in claim 1, further characterized in that ultraviolet light treats blood containing COVID-19 and/or pathogens.

* * * * *